United States Patent [19]
Greenwood et al.

[11] Patent Number: 5,457,101
[45] Date of Patent: Oct. 10, 1995

[54] THIENO[1,5]BENZOIDIAZEPINE USE

[75] Inventors: Beverley Greenwood, Oklahoma City, Okla.; David L. G. Nelson, Carmel, Ind.

[73] Assignee: Eli Lilly and Company, Indianapolis, Ind.

[21] Appl. No.: 253,658

[22] Filed: Jun. 3, 1994

[51] Int. Cl.⁶ .................................................. A61K 31/55
[52] U.S. Cl. ............................................................ 514/220
[58] Field of Search ................................................ 514/220

[56] References Cited

U.S. PATENT DOCUMENTS 5,229,382  7/1993  Chakrabarti et al. .................. 514/220

Primary Examiner—Jerome D. Goldberg
Attorney, Agent, or Firm—MaCharri Vorndran-Jones; David E. Boone; Gerald V. Dahling

[57] ABSTRACT

The compound 2-methyl-4-(4-methyl-1-piperazinyl)-10H-thieno-[2,3-b][1,5]benzodiazepine, or an acid salt thereof, has pharmaceutical properties, and is of particular use in the treatment of certain gastrointestinal disorders.

4 Claims, No Drawings

THIENO[1,5]BENZOIDIAZEPINE USE

FIELD OF THE INVENTION

This invention relates to a new method of use for 2-methyl-4-(4-methyl-1-piperazinyl)-10H-thieno-[2,3-b] [1,5] benzodiazepine for treating certain gastrointestinal conditions.

BACKGROUND OF THE INVENTION

The compound 2-methyl-4-(4-methyl-1-piperazinyl)-10H-thieno-[2,3-b][1,5]benzodiazepine, can be useful for treating certain gastrointestinal conditions. One such gastrointestinal condition is irritable bowel syndrome which is characterized by abdominal pain, alteration of bowel habits, or a combination of the two. Irritable bowel syndrome is expensive and afflicts between 14% to 22% of the population. *Gastroenterology*, 591–595, 100 (1991).

SUMMARY OF THE INVENTION

This invention provides a method for treating a mammal, suffering from or susceptible to a Functional Bowel Disorder, which comprises administering an effective amount of 2-methyl- 4-(4-methyl-1-piperazinyl)-10H-thieno-[2,3 -b][1,5]benzodiazepine, or an acid addition salt thereof.

DETAILED DESCRIPTION OF THE INVENTION

Applicants have discovered that 2-methyl-4-(4-methyl-1-piperazinyl)-10H-thieno-[2,3-b] [1,5]benzodiazepine can be useful in the treatment of Functional Bowel Disorders and related gastric hypermotility disorders. The compound has the following chemical structure:

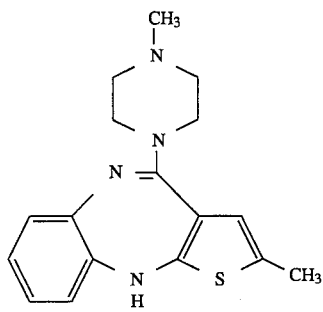

The 2-methyl-4-(4-methyl-1-piperazinyl)-10H-thieno-[2,3-b][1,5]benzodiazepine is described in U.S. Pat. No. 5,229,382 which is hereby incorporated by reference in its entirety.

As used herein, the term "mammal" shall refer to the mammalia class of higher vertebrates. The term "mammal" includes, but is not limited to, a human.

The term "treating" as used herein includes prophylaxis of the named condition or amelioration or elimination of the condition once it has been established.

As used herein the term "Functional Bowel Disorder" refers to a functional gastrointestinal disorder manifested by (1) abdominal pain and/or (2) symptoms of disturbed defecation (urgency, straining, feeling of incomplete evacuation, altered stool form [consistency] and altered bowel frequency/timing) and/or (3) bloating (distention). The term "Functional Bowel Disorder" includes but is not limited to irritable bowel syndrome, hypermotility, ichlasia, hypertonic lower esophogeal sphinctor, tachygastria, constipation, hypermotility associated with irritable bowel syndrome.

Functional Bowel Disorders are characterized by abnormal bowel function without detectable structural abnormalities. Abnormal bowel function includes diarrhea, constipation, mucorrhea, and pain or discomfort over the course of the sigmoid colon. Such disorders are influenced by psychological factors and stressful life situations.

The Functional Bowel Disorder, Irritable Bowel Syndrome (IBS), is one of the most commonly encountered gastrointestinal disorders. Between 20% and 50% of patients referred to gastrointestinal clinics suffer from IBS. Symptoms of IBS occur in approximately 14% of otherwise apparently healthy people. IBS is a complex condition, in part because it is not a disease but a syndrome composed of a number of conditions with similar manifestations.

The compound 2-methyl-4-(4-methyl-1-piperazinyl)-10H-thieno-[2,3-b][1,5]benzodiazepine has antimuscarinic activity, 5-$HT_{2B}$ receptor activity, and is denoted for use in the treatment of certain gastrointestinal conditions. Thus, the compound is useful for the treatment of Functional Bowel Disorders including, but not limited to, irritable bowel syndrome, gastric hypermotility, and related conditions.

More preferably 2-methyl-4-(4-methyl-1-piperazinyl)-10H-thieno-[2,3-b][1,5]benzodiazepine is used for the treatment of irritable bowel syndrome or gastric hypermotility disorder. Most preferably, 2-methyl- 4-(4-methyl-1-piperazinyl)-10H-thieno-[2,3-b] [1,5]benzodiazepine is used for the treatment of irritable bowel syndrome.

The preparation of 2-methyl-4-(4-methyl-1-piperazinyl)-10H-thieno-[2,3-b][1,5]benzodiazepine is described in U.S. Pat. No. 5,229,382, incorporated by reference supra.

The 2-methyl-4-(4-methyl-1-piperazinyl)-10H-thieno-[2,3-b][1,5]benzodiazepine can be used for the treatment of gastrointestinal conditions both in the free base and acid addition salt forms. The acid addition salts are preferably the pharmaceutically acceptable, non-toxic addition salts with suitable acids, such as those of inorganic acids, for example hydrochloric, hydrobromic, nitric, sulphuric or phosphoric acids, or of organic acids, such as organic carboxylic acids, for example glycollic, maleic, hydroxymaleic, fumaric, malic, tartaric, citric or lactic acid, or organic sulphonic acids for example methane-sulphonic, ethanesulphonic, 2-hydroxyethanesulphonic, toluene-p-sulphonic or naphthalene-2-sulphonic acid.

As mentioned above, 2-methyl-4-(4-methyl-1-piperazinyl)- 10H-thieno-[2,3-b][1,5]benzodiazepine has useful central nervous system activity. This activity has been demonstrated in animal models using well-established procedures. In addition, 2-methyl-4-(4-methyl- 1-piperazinyl)-10H-thieno-[2,3-b] [1,5]benzodiazepine has been found to have a favorable profile of activity in a number of in vitro binding assays, designed to measure the degree of binding to neural receptors.

The compound has an $IC_{50}$ of less than 1 μM in the $^3$H-QNB binding assay described by Yamamura, H. I. and Snyder, S. H. in Proc. Nat. Acad. Sci. U.S.A. 71 1725 (1974) indicating that it has antimuscarinic-anticholinergic activity. In addition, the compound shows its greatest activity at the 5-HT-2 receptor in that it displaces H-spiperone from binding sites in the rat frontal cortex (Peroutka, S. J. and Snyder, S. H. Mol. Pharmacol. 16 687 (1979)) at low nanomolar concentrations. The compound is also active at the 5-HT-1C receptor.

Radioligand Binding Studies

Membrane preparation from transformed cells. Suspension cells expressing the cloned human 5-HT$_{2B}$ receptor were processed as previously described for the cloned rat 5-HT2B receptor. Kursar, J. D., D. L. Nelson, D. B. Wainscott, M. L. Cohen, and H. Baez, Mol. Pharmacol. 42: 549–557 (1992). The cells were harvested by centrifugation at 2,200×g for 15 min at 4° C. Membranes for the binding assays were prepared by vortexing the pellet in 50 mH Tris-HCl, pH 7.4 (0.5×10$^9$ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, using a Tissumizer (Tekmar, Cincinnati, Ohio), setting of 65 for 15 seconds.

[$^3$H]5-HT binding studies. Binding assays were automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [$^3$H]5-HT, pargyline, CaCl$_2$, and L-ascorbic acid. Final concentrations of pargyline, CaCl$_2$ and L-ascorbic acid were 10 μM, 3 mM and 0.1%, respectively. Tubes were incubated at 37° C. for 15 min (binding equilibria were verified for both of these conditions), then rapidly filtered using a Brandel cell harvester (Model HB-48R; Brandel, Gaithersburg, Md.) through Whatman GF/B filters which were presoaked in 0.5% polyethylenimine and precooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman LS-6000 IC, Beckman Instruments). Saturation curves for [$^3$H]5-HT binding were determined for best fit to a one-site or a two-site binding model using a partial F-test. De Lean, A., A. A. Hancock, and R. J. Lefkowitz, Mol. Pharmacol. 21: 5–16 (1981). The following equation was used for a one-site binding model, $$\text{Bound} = \frac{B_{max} \times [L]}{K_d + [L]}$$

where Bound=amount of [$^3$H]5-HT specifically bound, $B_{max}$= maximum number of binding sites, $K_d$=equilibrium dissociation constant and [L]=free concentration of [$^3$H]5-HT, or a two-site binding model, $$\text{Bound} = \frac{B_{max1} \times [L]}{K_{d1} + [L]} + \frac{B_{max2} \times [L]}{K_{d2} + [L]}$$

where Bound=amount of [$^3$H]5-HT specifically bound, $B_{max1}$= maximum number of high affinity binding sites, $B_{max2}$= maximum number of low affinity binding sites, $K_{d1}$= equilibrium dissociation constant for the high affinity site, $K_{d2}$=equilibrium dissociation constant for the low affinity site and [L]=free concentration of [$^3$H]5-HT. The IC$_{50}$ values from the competition assays, the binding parameters for the IP$_3$ standard curve and the EC$_{50}$ and E$_{max}$ values from the IP$_3$ assays were determined by nonlinear regression analysis of four parameter logistic equations (Systat, Systat Inc, Evanston, Ill.). De Lean, A., A. A. Hancock, and R. J. Lefkowitz, Mol. Pharmacol. 21: 5–16 (1981). The IC$_{50}$ values were converted to K$_i$ values using the Cheng-Prusoff equation. Cheng, Y., and W. H. Prusoff, Biochem. Pharmacol. 22: 3099–3108 (1973).

Assay Methods 5-HT$_{2B}$ receptor in tissue in vitro:

Male Wistar rats (150–375 g; Laboratory Supply, Indianapolis, Ind.) are sacrificed by cervical dislocation, and longitudinal section of the stomach fundus are prepared for in vitro examination. Four preparations are obtained from one rat fundus. Cohen, M. L. and J. Pharmacol. Exp. Ther. 233:75–79 (1985). Tissues are mounted in organ baths containing 10 mL of modified Krebs' solution of the following composition (millimolar concentrations): NaCl, 118.2, KCl, 4.6; CaCl$_2$.H$_2$O, 1.6; KH$_2$PO$_4$, 1.2; MgSO$_4$, 1.2; dextrose, 10.0; and NaHCO$_3$, 24.8. Tissue bath solutions are maintained at 37° C. and equilibrated with 95% O$_2$ and 5% CO$_2$. Tissues are placed under optimum resting force (4 g) and are allowed to equilibrate for approximately 1 hour before exposure to the test compound. Isometric contractions are recorded as changes in grams of force on a Beckman Dynograph with Statham UC-3 transducers.

Determination of Apparent Antagonist Dissociation Constant

Noncumulative contractile concentration-response curves for serotonin and other agonists in the fundus are obtained by a stepwise increase in concentration after washing out the preceding concentrations every 15–20 minutes. Each agonist concentration remains in contact with the tissue for approximately 2 minutes and maximum response to each compound concentration is measured. ED$_{50}$ values are taken as the concentration of agonist that produces half-maximal contraction. After control responses are obtained, tissues are incubated with an appropriate concentration of buffer or antagonist for 1 hour. Responses to serotonin are then repeated in the presence of an antagonist. Concentration responses utilize only one agonist and one antagonist concentration per tissue. In general, successive agonist responses in the presence of buffer treatment are unaltered average dose ratio was 1.28+ /–0.21).

Apparent antagonist dissociation constants (K$_B$) are determined for each concentration of antagonist according to the following equation:

$$K_{B=[B]/}(\text{dose ratio}-1)$$

where [B] is the concentration of the antagonist and dose ratio is the ED$_{50}$ of the agonist in the presence of the antagonist divided by the control ED$_{50}$. Generally, parallel shifts in the concentration-response curves occur in the presence of antagonists. The results are expressed as the negative logarithm of the K$_B$ (i.e., –log K$_B$). Calculations are completed using known methods.

Functional In Vitro Assay

Sprague-Dawley rats (200–250 g; Laboratory Supply, Indianapolis, Ind.) are sacrificed by cervical dislocation and 8 cm segment of distal colon is removed and washed in ice cold modified Kreb's solution of the following composition (millimolar): NaCl, 118.2; KCl, 4.6; CaCl$_2$. H$_2$O, 1.6; KH$_2$PO$_4$, 1.2; MgSO$_4$, 1.2; dextrose, 10.0; and NaHCO$_3$, 24.8. The colon is mounted on a glass rod and the longitudinal muscle layer with attached myenteric plexi is removed and mounted in organ baths, containing above described Kreb's solution maintained at 37° C. and equilibrated with 95% O$_2$ and 5% CO$_2$. Tissues are placed under 2 g tension and allowed to stabilize for 1 hour. Isometric contractions are recorded as changes in grams of force using grass FTO3 transducers and MI$^2$- computerized dynograph system. Cumulative concentration-response curves for serotonin were obtained by a stepwise increase in concentration after washing out the preceding concentration for 10–15 minutes. Each agonist concentration remains in contact with the tissue for 5 minutes. Maximum response to each concentration is determined and digitized. EC$_{50}$ values are taken as the concentration of agonist that produced half maximal contraction. After control responses are obtained, tissues are incubated with an appropriate concentration of antagonist for 15 minutes. Response to serotonin are then repeated in the presence of an antagonist. Concentration-response utilizes only one concentration of antagonist per tissue. Apparent antagonist dissociation constants (K$_B$) are determined for each concentration of antagonist according to the following equation:

$$K_{B=[B]}/(dose\ ratio-1)$$

where [B] is the concentration of the antagonist and dose ratio is the ED$_{50}$ of the agonist in the presence of antagonist divided by the control ED$_{50}$. The results are expressed as the negative logarithm of the K$_B$ (i.e., –log K$_B$) (Br. J. Pharmacol. Methods 4:4165, (1980).

Studies indicate that compounds which are 5-HT$_{2B}$ receptor antagonists are potent competitive inhibitors of serotonin-induced contraction of the colon. Such compounds can act to normalize gastrointestinal motility and be useful in the treatment of Functional Bowel Disorders.

The profile of activity observed in the in vitro receptor binding assays indicates that the compound is effective for the treatment of Functional Bowel Disorders.

The 2-methyl-4-(4-methyl-1-piperazinyl)-10H-thieno-[2,3-b][1,5]benzodiazepine compound is effective over a wide dosage range, the actual dose administered being dependent on the condition being treated. For example, in the treatment of adult humans, dosages of from 0.25 to 30 mg, preferably from 1 to 20 mg, per day may be used. A once a day dosage is normally sufficient, although divided doses may be administered. For treatment of gastrointestinal disorders, a dose range of from 1 to 20 mg, preferably 2.5 to 15 mg per day is suitable. In studies using radiolabelled 2-methyl- 4-(4-methyl-1-piperazinyl)-10H-thieno-[2,3 -b] [1,5] benzodiazepine, residues have been detected in the saliva and thus the compound can potentially be monitored in patients to assess compliance.

The 2-methyl-4-(4-methyl-1-piperazinyl)-10H-thieno[2,3-b][1,5]benzodiazepine compound will normally be administered orally or by injection and, for this purpose, it is usually employed in the form of a pharmaceutical composition.

Accordingly, pharmaceutical compositions comprising 2-methyl-4-(4-methyl-1-piperazinyl)-10H-thieno[ 2,3-b][1, 5]benzodiazepine, or a pharmaceutically acceptable acid addition salt thereof, as active ingredient associated with a pharmaceutically acceptable carrier may be prepared. In making the compositions of the invention conventional techniques for the preparation of pharmaceutical compositions may be used. For example, the active ingredient will usually be mixed with a carrier, or diluted by a carrier, or enclosed within a carrier which may be in the form of a capsule, sachet, paper or other container. When the carrier serves as a diluent, it may be solid, semi-solid or liquid material which acts as a vehicle, excipient or medium for the active ingredient. The active ingredient can be adsorbed on a granular solid container for example in a sachet. Some examples of suitable carriers are lactose, dextrose, sucrose, sorbitol, mannitol, starches, gum acacia, calcium phosphate, alginates, tragacanth, gelatin, syrup, methyl cellulose, methyl- and propyl-hydroxy-benzoate, talc, magnesium stearate or mineral oil. The compositions of the invention may, if desired, be formulated so as to provide quick, sustained or delayed release of the active ingredient after administration to the patient.

Depending on the method of administration, the compositions for the treatment of gastrointestinal conditions may be formulated as tablets, capsules, injection solutions for parenteral use, gel or suspension for transdermal delivery, suspensions or elixirs for oral use or suppositories. Preferably the compositions are formulated in a unit dosage form, each dosage containing from 0.25 to 30 mg, more usually 1 to 20 mg, of the active ingredient. When a sustained release formulation is desired, the unit dosage form may contain from 0.25 to 200 mg of the active ingredient. A preferred formulation of the invention is a capsule or tablet comprising 0.25 to 30 mg or 1 to 20 mg of active ingredient together with a pharmaceutically acceptable carrier therefor. A further preferred formulation is an injection which in unit dosage form comprises 0.25 to 30 mg or 1 to 20 mg of active ingredient together with a pharmaceutically acceptable diluent therefor.

EXAMPLE 1

A pulvule formulation is prepared by blending the active with silicone starch, and filling it into hard gelatin capsules.

|  | Per 300 mg capsule |
|---|---|
| 2-methyl-4-(4-methyl-1-piperazinyl)-10H-thieno-[2,3-b][1,5]benzodiazepine | 5.0 mg |
| Silicone | 2.9 mg |
| Starch flowable | 292.1 mg |

EXAMPLE 2

A tablet formulation is made by granulating the active with appropriate diluent, lubricant, disintegrant and binder and compressing

| 2-methyl-4-(4-methyl-1-piperazinyl)-10H-thieno-[2,3-b][1,5]benzodiazepine | 5.0 mg |
|---|---|
| Magnesium stearate | 0.9 mg |
| Microcrystalline cellulose | 75.0 mg |
| Povidone | 15.0 mg |
| Starch, directly compressible | 204.1 mg |

EXAMPLE 3

An aqueous injection of active compound is prepared as a freeze-dried plug, for reconstitution with diluent in a suitable, sterile 25 ml vial before use (to a total volume of 10 ml). The 2-methyl-4-(4-methyl-1-piperazinyl)-10H-thieno-[ 2,3-b][1,5]benzodiazepine, mannitol, N hydrochloric acid and/or N sodium hydroxide to adjust pH to 5–5.5.

| 2-methyl-4-(4-methyl-1- | 20.0 mg |

| | |
|---|---|
| piperazinyl)-10H-thieno-[2,3-b][1,5]benzodiazepine | |
| Mannitol | 20.0 mg |
| N Hydrochloric acid and/or N sodium hydroxide to adjust pH to 5–5.5. | |

EXAMPLE 4

A controlled release injection for intramuscular injection is formed from a sterile suspension of micronised active in an oleaginous vehicle.

| | |
|---|---|
| 2-methyl-4-(4-methyl-1-piperazinyl)-10H-thieno-[2,3-b][1,5]benzodiazepine | 65.0 mg |
| Aluminium stearate | 0.04 mg |
| Sesame oil | 2 ml |

EXAMPLE 5

A capsule formulation is prepared by blending the active with silicone starch and starch, and filling it into hard gelatine capsules.

| | Per 290 mg capsule |
|---|---|
| 2-methyl-4-(4-methyl-1-piperazinyl)-10H-thieno[2,3-b][1,5]benzodiazepine | 2.5 mg |
| Starch flowable with 0.96% silicone 220 | 217.5 mg |
| Starch flowable | 70.0 mg |

We claim:

1. A method for treating a mammal, suffering from a Functional Bowel Disorder, which comprises administering an effective amount of 2-methyl- 4-(4-methyl-1-piperazinyl)-10H-thieno-[2,3-b] [1,5]benzodiazepine, or an acid addition salt thereof.

2. A method of claim 1 for treating a mammal, suffering from a Functional Bowel Disorder selected from the group consisting of irritable bowel syndrome, hypermotility, ichlasia, hypertonic lower esophogeal sphinctor, tachygastria, constipation, and hypermotility associated with irritable bowel syndrome.

3. A method of claim 2 for treating a mammal, suffering from a Functional Bowel Disorder selected from the group consisting of irritable bowel syndrome and hypermotility associated with irritable bowel syndrome.

4. A method of claim 1 wherein the effective amount is from 1 to 20 mg per day of 2-methyl-4-(4-methyl- 1-piperazinyl)-10H-thieno-[2,3-b] [1,5]benzodiazepine, or an acid addition salt thereof.

* * * * *